United States Patent [19]

Potter et al.

[11] Patent Number: 4,747,401
[45] Date of Patent: * May 31, 1988

[54] SURGICAL ADHESIVE DRESSING

[75] Inventors: William D. Potter, Bishops Stortford; David A. Rawlings, Stansted Mountfitchet, both of United Kingdom

[73] Assignee: Smith and Nephew Associated Companies p.l.c., United Kingdom

[*] Notice: The portion of the term of this patent subsequent to Jun. 17, 2003 has been disclaimed.

[21] Appl. No.: 926,194

[22] Filed: Nov. 3, 1986

Related U.S. Application Data

[63] Continuation of Ser. No. 794,854, Nov. 4, 1985, abandoned, which is a continuation of Ser. No. 541,324, filed as PCT GB83/00104 on Apr. 18, 1983, published as WO83/03549 on Oct. 27, 1983, Pat No. 4,595,001.

[30] Foreign Application Priority Data

Apr. 8, 1982 [GB] United Kingdom ................ 8219541

[51] Int. Cl.$^4$ .............................................. A61L 15/00
[52] U.S. Cl. ..................................... 128/156; 604/369
[58] Field of Search ....................... 128/155, 156, 320; 604/369, 366, 370

[56] References Cited

U.S. PATENT DOCUMENTS

| | | |
|---|---|---|
| 2,430,860 | 11/1947 | Cairns . |
| 2,647,100 | 7/1953 | Salditt . |
| 2,871,218 | 1/1959 | Schollenberger ..................... 528/83 |
| 3,121,021 | 2/1964 | Copeland . |
| 3,483,018 | 12/1969 | Waldman . |
| 3,520,949 | 7/1970 | Shepherd et al. . |
| 3,526,224 | 6/1967 | Potts . |
| 3,579,628 | 5/1971 | Gander . |
| 3,645,835 | 2/1972 | Hodgson ............................ 128/156 |
| 3,821,136 | 6/1974 | Hudgin et al. . |
| 3,822,238 | 7/1974 | Blair et al. . |
| 3,975,350 | 8/1976 | Hudgin et al. ........................ 128/127 |
| 4,061,618 | 12/1977 | Stanley . |
| 4,156,066 | 5/1979 | Gould . |
| 4,156,067 | 5/1979 | Gould . |
| 4,413,621 | 11/1983 | McCracken et al. ............... 128/156 |
| 4,452,845 | 6/1984 | Lloyd et al. . |
| 4,595,001 | 6/1986 | Potter et al. ........................ 128/156 |

FOREIGN PATENT DOCUMENTS

| | | |
|---|---|---|
| 0006714 | 6/1979 | European Pat. Off. . |
| 0028452 | 9/1980 | European Pat. Off. . |
| 0035399 | 9/1981 | European Pat. Off. . |
| 0050035 | 10/1981 | European Pat. Off. . |
| 0051935 | 5/1982 | European Pat. Off. . |
| 0090564 | 5/1983 | European Pat. Off. . |
| 0091800 | 10/1983 | European Pat. Off. . |
| 2440380 | 6/1978 | France . |
| 648733 | 10/1951 | United Kingdom . |
| 761840 | 11/1956 | United Kingdom . |
| 2093190 | 8/1982 | United Kingdom . |

OTHER PUBLICATIONS

European Search Report for Application No. 0,091,800, EP 83 30 1983.

*Primary Examiner*—C. Fred Rosenbaum
*Assistant Examiner*—Denise Whelton
*Attorney, Agent, or Firm*—Jacobs & Jacobs

[57] ABSTRACT

A surgical dressing which consists essentially of a film which carries an adhesive layer for securing the dressing to the body characterized in that (a) the film is continuous and comprises a polymer which in contact with water has a higher MVP than when in contact with moisture vapor but not water, (b) the adhesive layer is adapted to allow access of water to the film when water is in contact with the adhesive layer so that said surgical dressing has a MVP of not less than 2500 g/m$^2$ when the adhesive layer is in contact with water and has a MVP of not more than 2000 g/m$^2$ when the adhesive is in contact with moisture vapor but not water; whereby the dressing is suitable for use on exuding wounds and on non-exuding wounds.

10 Claims, No Drawings

SURGICAL ADHESIVE DRESSING

This is a continuation of Ser. No. 794,854, filed Nov. 4, 1985, which is a continuation of Ser. No. 541,324, filed as PCT GB83/00104 on Apr. 18, 1983, published as WO83/03549 on Oct. 27, 1983, now U.S. Pat. No. 4,595,001, issued on 6/17/86.

The present invention relates to adhesive dressings for use on the human body. More particularly this invention relates to adhesive surgical dressings suitable for use on both exuding wounds and non-exuding wounds.

Moisture vapour permeable thin films coated with adhesive were disclosed in British Pat. No. 1,280,631 and U.S. Pat. No. 3,645,835 as being suitable for use as surgical dressings. In recent years one such film has come to prominence under the trade mark "Op-Site" and has found use as a surgical dressing, for example for covering burns, donor sites, surgical incisions, intravenous catheter sites and the like. The known dressings have proved useful because they keep out bacteria owing to the microscopically continuous nature of the film and adhesive layer but do not cause maceration of the skin to which it is applied because both the film and the adhesive layer have high moisture vapour permeability (MVP). One problem with presently available high MVP dressings is that the MVP is not high enough for some uses such as covering exuding wounds when an unsightly blister can occur. However it has not been thought practicable simply to increase the MVP of the product overall since this would lead to drying out of some wounds with a consequent reduction in the rate of healing. It has now been discovered that it is possible to alleviate the known disadvantage of conventional surgical dressings by providing dressings which transmit substantially more moisture vapour when in contact with a wetter wound than they do when in contact with a dryer wound.

Accordingly the present invention provides a surgical dressing which consists essentially of a film which carries an adhesive layer for securing the dressing to the body characterised in that (a) the film is continuous and comprises a polymer which in contact with water has a higher MVP than when in contact with moisture vapour but not water (b) the adhesive layer is adapted to allow access of water to the film when water is in contact with the adhesive layer so that (c) said surgical dressing has a MVP of not less than 2500 g/m$^2$ when the adhesive layer is in contact with water and has an MVP of not more than 2000 g/m$^2$ when the adhesive is in contact with moisture vapour but not water; whereby the dressing is suitable for use on exuding wounds and on non-exuding wounds.

When used herein with reference to "contact" the term "water" means liquid water (as opposed to moisture vapour) unless otherwise specified. When used herein MVP units are g/m$^2$/24 hrs/37° C./100-10% relative humidity and are generally abbreviated to g/m$^2$.

Suitable test methods for determining the MVP of a dressing or its components are set forth in the Description hereinafter. When MVP values quoted thereinafter are referred to as "wet-MVP" they refer to values obtained with the adhesive face in contact with water and when referred to as "dry-MVP" they refer to values obtained with the adhesive face not in contact with water.

More suitably the dressing of this invention will have a wet-MVP of not less than 3000 g/m$^2$, most suitably will have a wet-MVP of not less than 3200 g/m$^2$ and preferably will have a wet-MVP of not less than 5000 g/m$^2$.

More suitably the dressing of this invention will have a dry-MVP of not more than 1500 g/m$^2$, most suitably will have a dry-MVP of not more than 1400 g/m$^2$ and preferably will have a dry-MVP of not more than 1200 g/m$^2$.

The film used in this invention may comprise any synthetic or modified natural polymer which has a sufficiently higher wet-MVP than dry-MVP to produce the desired MVP parameters in the dressing. The method set out in the Descriptions may be employed to determine whether the film material exhibits the desired MVP when in contact with water. Most aptly the film comprises a synthetic polymer although modified natural polymers such as regenerated cellulose or cellulose acetate may be employed if sufficiently plasticised to conform to the movements of the body when adhered thereto. Preferably the synthetic polymer employed is an elastomer so that it readily conforms to the movement of the skin when the dressing is in use.

Most suitably the film used in this invention will be hydrophilic, that is will absorb water when immersed therein. Aptly the film material when hydrated will contain 5% to 50% water (w/w at 20° C.), more aptly from 10% to 40% of water and favourably from 20% to 30% of water.

Suitable hydrophilic film material will include polyurethanes, polyether polyamide block copolymers, polyether polyester block copolymers, cross-linked polyvinyl alcohols, acrylic copolymers, polyamides, regenerated cellulose, cellulose acetate and the like, provided said film material are highly conformable (whether per se or by plasticisation) and that the material used most suitably has the preceeding water contents when hydrated.

The film employed will be a continuous film, that is it will be free of holes (whether microporous or macroporous) which allow the passage of bacteria.

The desirable properties of this invention may be best obtained by employing a film of hydrophilic polyurethane in combination with an adhesive layer adapted to allow access of water to the film when water is presented to the adhesive face of the dressing.

Most suitably the film will be from 15 to 80 microns thick, will more usually be from 20 to 60 microns thick and will preferably be from 25 to 50 microns thick, for example 30, 35 or 40 microns thick.

Aptly the film will be formed from a hydrophilic polyurethane which when hydrated contains from 5% to 50% of water, more aptly from 10% to 40% of water and favourably from 20% to 30% water.

In order to enable visual observation of the wound it is desirable for the film use in this invention to be transparent. This in turn requires that the film should be capable of being self supporting, that is sufficiently coherent when wet or dry to be used without recourse to additional support such as a fabric, for example a gauze, net or the like. It has been found that polyether polyurethanes are particularly suitable for use in the formation of such films. Favoured polyether polyurethanes are essentially free of reactive substituents such as hydroxyl or carboxyl groups. It has been found that certain apt polyurethanes for use in this invention are random polymers containing units derived from diolic compounds and di-isocyanates.

Suitable polyurethanes are those whose ether units in the hydrophilic polyurethane will be notionally derivable from ethylene diol and a propylene or butylene diol; that is, they will contain $CH_2CH_2O-$ units and $-CH_2CH_2CH_2O-$, $CH_2CH(CH_3)O-$ or $-CH_2CH_2CH_2CH_2O-$ units. Most aptly the ether units in the polyurethane will contain $-CH_2CH_2O-$ and $-CH_2CH(CH_3)O-$ or $-(CH_2)_4O-$ mixtures thereof of which poly $-CH_2CH(CH_3)O-$ blocks are preferred. Desirably the mole ratio of poly(ethylene glycol) to poly[(prop or but)ylene glycol] derivable blocks present in the hydrophilic polyurethanes vary between 1:1 to 1:30, more suitably from 1:2 ro 1:10 and preferably from 1:2.5 to 1:4. The molecular weights of these blocks is aptly from 600 to 60,000 and favourably from 900 to 4000, for example 1000 to 2000.

Most aptly the hydrophilic polyurethane for use in this invention will contain resides of aliphatic diols of up to 10 carbon atoms and more suitably up to 4 carbon atoms (of which ethane diol is preferred) as chain extenders wherein the mole ratio of diol to polyglycol used in the preparation of the polymer is from 3:1 to 1:4, more aptly 5:2 to 1:3 and preferably from 2:1 to 1:2.

The hydrophilic polyurethane will contain sufficient di-isocyanate resides to produce the water contents set forth hereinbefore when the polymer is hydrated.

Most aptly the hydrophilic polyurethane for use in this invention will contain di-isocyanate residues which may be residues of aromatic or aliphatic di-isocyanates such as 4,4'-diphenylmethane di-isocyanate, toluene di-isocyanate, 1,6-hexamethylene di-isocyanate, 4,4'-dicyclohexylmethane di-isocyanate or the like. Favoured di-isocyanates for use in the hydrophilic polyurethane of this invention are 4,4'-dicyclohexylmethane di-isocyanate (which is preferred) and 4,4'-diphenylmethyl di-isocyanate.

Less aptly than using aliphatic diol chain extenders, the hydrophilic polyurethane may employ equivalent quantities of aliphatic diamine or aliphatic amineol chain extenders of which ethylene diamine is preferred. Similarly somewhat less aptly than using aliphatic diol chain extenders, the hydrophilic polyurethane may employ an aromatic diamine such as phenylenediamine, benzidine or diaminodiphenylmethane.

Less aptly than using a mixture of poly(ethylene glycol) and poly[(prop or but)ylene glycol] derived blocks, the hydrophilic polyurethane may employ poly(ethylene-glycol) derived blocks alone together with a higher proportion of chain extender and di-isocyanate.

Normally and preferably the hydrophilic polyurethane used in the devices of this invention is essentially a single type of polymer (a product of the polymerisation of the same materials) although blends may be employed to form the hydrophilic polyurethane if desired.

The adhesive layer present on the body contacting surface of the film is favourably an interrupted layer so that areas of the film are free of adhesive, aptly 20 to 75% of the film is free of adhesive, more aptly 30 to 70% of the film face is free of adhesive and preferably 40 to 60% of the film face is free of adhesive. The use of an interrupted layer in such a manner has been found to be highly beneficial in allowing the desirable variability of MVP to be achieved.

The adhesive is generally employed at a mass per unit area of 10 to 80 g/m², more aptly 20 to 45 g/m² and favourably from 25 to 35 g/m².

The adhesive may be applied around the periphery of the dressings, in lines over the face of the dressing (parallel, at right angles, forming diamond pattern or the like) or in combinations of such systems.

The adhesive is preferably one which itself transmits water vapour, for example one which if present as a film 25 microns thick would have a MVP of at least 300 g/m², more suitably at least 500 g/m² and preferably at least 700 g/m². Such permeabilities may be achieved by using a non-porous or porous (including microporous) pattern spread adhesive but generally it is preferred to employ a non-porous pattern spread adhesive. Suitable adhesives include polyvinyl ethyl ether adhesive and acrylate surgical adhesives. Preferred adhesives include polyacrylates which have a K value of 90 to 110 and contain 16% to 62% of n-butylacrylate residues, 80% to 34% of 2-ethylhexyl acrylate residues and 4% to 10% of acrylic acid residues.

All % terms herein are expressed on wt/wt basis.

Very desirably the polymer contains 34% to 62% n-butyl acrylate residues. Very desirably the polymer contains 62% to 34% of 2-ethylhexyl acrylate residues. Very desirably the polymer contains 4% to 8% of acrylic acid residues.

More suitably the polymer contains 45% to 55% n-butyl acrylate residues. More suitably the polymer contains 45% to 55% of 2-ethylhexylacrylate residues. More suitably the polymer contains 5% to 7% acrylic acid residues. Preferably the polymer contains 47% n-butyl acrylate residues. Preferably the polymer contains 47% 2-ethylhexyl acrylate residues. Preferably the polymer contains 6% acrylic acid residues.

The adhesive polymer will not have a high degree of crosslinking; that is, the polymer is effectively linear. This results in the adhesive polymer being capable of being dissolved in solvent even after tunnel spreading.

The K value of the polymer will be within the range 90 to 100, most suitably 91 to 106 and is preferably within the range 95 to 105 and most preferably within the range 96 to 100. (K values may be determined by the published method of DIN 53726). (K values of 90, 95, 105 and 110 are equivalent to inherent viscosities of 1.7, 1.9, 2.5 and 3.0 dl/g). The polymers of this invention with these K-values have acceptable cohesive strength and acceptable wet-stick. These desirable properties are particularly apparent when the adhesive polymer has a wider molecular weight distribution.

In another aspect there is provided a solution in acetone or ethyl acetate of an adhesive polyacrylate wherein the solution contains 20 to 45% of adhesive polyacrylate.

In general, the polymer is provided in the form of a solution such as acetone, ethyl acetate or the like. A 20 to 45% solution in acetone is a favored form, for example a 30 to 40% solution.

The following preparative examples illustrate the preparation of adhesives useful in the present invention:

PREPARATIVE EXAMPLE A

Preparation of Acrylic Adhesive Formulation

| Reagents: | | | |
|---|---|---|---|
| | Glacial Acrylic Acid | 75.2 g | (75.2 cm³) |
| | 2-ethylhexylacrylate | 589 g | (665 cm³) |
| | n-butylacrylate | 589 g | (665 cm³) |

-continued

| | | |
|---|---|---|
| Benzoyl peroxide | 0.9 g | dissolved in 30 cm³ acetone |
| Acetone | 1412 g | (1790 cm³) |

Apparatus: 5l resin flask fitted with an anchor type stirrer, condenser thermocouple holder, nitrogen inlet and dropping funnel; assembled on a steam bath.

Procedure: 80% of the acetone together with ⅓ of the monomers were charged into the resin flask and purged with nitrogen for 10 minutes. Steam was turned on contents heated to gentle reflux. 5 cm³ of the benzoyl peroxide catalyst was added and the reactants allowed to react for 3 hours. The rest of the reactants were charged to the pot as shown in the table below.

| Reactants | Reaction time (hrs) | Pot Temp. (°C.) |
|---|---|---|
| 1/3M + 1/6C | 0-3 | 60°-57° |
| +1/6M + 1/6C | 3-5 | 58.5° |
| +1/6M + 1/6C | 5-6¾ | 60° |
| +1/6M + 1/6C | 6¾-8¼ | 60° |
| +1/6M + 1/6C | 8¼-9¼ | 60° |

On complete addition of monomers, the 5l resin flask was removed from the steam bath and was assembled on a constant temperature bath kept at 60° C. (±1). 20% of the acetone and the remainder of the catalyst (1/6) was added to the pot and the reaction mixture was allowed to react for a further 14¾ hours, i.e. total reaction time=24 hours.

Assay: (Residual monomer content less than 1%; K value=100; the cohesive strength of the adhesive was sufficient to prevent cohesive failure on skin under wet conditions).

PREPARATIVE EXAMPLE B

A further amount of acetone was added to the mixture of Example A to give a solution containing 33% of the adhesive polyacrylate.

The procedure is described in the following preparative examples:

EXAMPLE I

General Preparative Procedure

The required quantities of polyglycol, chain extenders (aliphatic diol or diamine) and water were warmed to approximately 80° C. and mixed completely in a covered beaker. The required quantity of di-isocyanate was added to the warm mixture and the total mass stirred until a clear solution resulted. The temperature was allowed to fall to 70° C. at which point the appropriate weight of catalyst was added from a syringe and the mixture stirred continuously until exothermic reaction reached 90° C. when it was poured quickly into a polypropylene tray and transferred immediately to an oven to cure for ½ hour at 100° C. The resulting foam was left at room temperature for at least 16 hours before cutting into pieces. (These pieces could be dissolved in a convenient solvent such as dichloromethane, methanol or mixtures thereof to form a solution suitable for coating objects).

Hydrophilic polyurethanes were prepared by the above procedure using polyethylene glycol 1540 (supplied by Union Carbide Corp.), polytetramethylene glycol 1010 (supplied by Quaker Oaks Corporation) ethane dial and 4,4'-dicyclohexylmethane di-isocyanate (supplied by Hylene W by Du Pont or Desmodur W by Bayer).

The materials also employed 0.25% water and 0.2% di-n-butyltinlaurate solution (Catalyst T-12).

| Mole ratio of polyglycol to ethandiol | Mole % polyethylene glycol 1540 to Polymeg | % Water |
|---|---|---|
| 1:0.5 | 5.0 | 10 |
| " | 10.0 | 16 |
| " | 20.0 | 16 |
| 1:1 | 5.0 | 8 |
| " | 10.0* | 11 |
| " | 12.5 | 15 |
| " | 15.0 | 18 |
| " | 15.0 | 17 |
| " | 17.5 | 23 |
| " | 20.0 | 30 |
| 1:1.5 | 7.6 | 9 |
| " | 10.0 | 13 |
| " | 14.0 | 19 |
| " | 17.0 | 20 |
| " | 20.0 | 26 |

*Formulation for this material is as follows:

| Material | |
|---|---|
| Polyethylene glycol 1540 | 9.15 g |
| Polymeg 1010 | 53.75 g |
| Ethane diol | 3.68 g |
| Water | 0.05 g |
| Hylene W | 33.37 g |
| Catalyst T-12 | 0.20 ml. |

Other hydrophilic polyurethanes were prepared from the following:

| Polyethylene glycol molecular weight | mole ratio of polyethylene glycol to Digol | % Water |
|---|---|---|
| 600 | 1:1.13 | 21 |
| 1000 | 1:1.13 | 34 |
| *1540 | 1:1.13 | 40 |
| 6000 | 1:1.13 | 48 |

*Formulation for this material is as follows:

| Material | |
|---|---|
| Polyethylene glycol 1540 | 42.49 g |
| Digol | 5.07 g |
| Water | 0.23 g |
| Hylene W | 29.50 g |
| Catalyst T-12 | 0.2 mls. |

| Polyethylene glycol molecular weight | Mole ratio of polyethylene glycol to Digol | % Water |
|---|---|---|
| 1000 | 1:0.33 | 38 |
| *4000 | 1:4.77 | 39 |
| 6000 | 1:7.75 | 44 |

*Formulation for this material is as follows:

| Material | |
|---|---|
| Polyethylene glycol 4000 | 62.59 g |
| Digol | 7.91 g |
| Water | 0.10 g |
| Hylene W | 32.10 g |
| Catalyst T-12 | 0.2 mls. |

| mole ratio of polyglycol to 1:2 diaminoethane | Mole ratio of polyethylene glycol to polymeg 1010 | % water |
|---|---|---|
| 1:1 | 1:19 | 6 |
| *1:1 | 1:9 | 12 |
| 1:1 | 1:4 | 22 |

*Formulation for this material is as follows:

| Material | |
|---|---|
| Polyethylene glycol 1540 | 9.16 g |
| Polymeg 1010 | 53.81 g |
| 1:2 Diaminoethane | 3.55 g |
| Water | 0.07 g |
| Hylene W | 33.41 g |
| Catalyst T-12 | 0.2 mls. |

(Amine extended polymer made by reacting isocyanate and polyglycol followed by reaction with amine).

EXAMPLE II

A mixture of the following:

| Polyethylene glycol 1540 | 15.4 g | (0.01 mole) |
| Polypropylene glycol 1025 | 30.75 g | (0.03 mole) |
| Ethane diol | 3.71 g | (0.06 mole) |
| Di-n-butyl tin di-laurate | 0.15 g | | was heated in a beaker to 50° C. on a hot plate with constant stirring. Hylene W (27.5 g; 0.11 moles) was added to the mixture which was stirred to 30 seconds when it became clear. The mixture was immediately poured into a mould (high density polythene) and placed in an oven at 70° C. for 1 hour. After removal from the oven the resulting hydrophilic polyurethane was left for at least 24 hours before use. (The material had a water uptake of about 26%).

EXAMPLE III

The polymer of Example II may be used in place of the polystyrene membrane in the sensor specifically described in U.S. Pat. No. 2,005,418.

EXAMPLE IV

Preparation of Hydrophilic Polyurethane on a 1 Kilogram Scale

Polyethylene glycol 1500 (193.9 g, 0.14 moles), polypropylene glycol 1025 (430.5 g, 0.42 moles) ethanediol (52.08 g, 0.84 moles) and catalyst T-12 (2.2 g) were weighed into a two liter glass beaker and placed into a fan assisted oven set at a temperature of 60° C. to melt the polyethylene glycol. When the polyethylene glycol had melted, the mixture was stirred well and Desmodur W (31.16 g, 1.6618 moles) added with continued stirring. The stirring was continued until the polymerisation mixture had changed from an opaque liquid to a clear liquid. At this point, the polymerisation mixture was poured into a polypropylene mould and placed in a fan assisted oven set at a temperature of 90° C. for one hour to cure. The elastomer obtained was allowed to cure for a further 24 hours at room temperature before use. The material has a water content after hydration of about 23%.

(This example uses a little more isocyanate than in Example II owing to the slightly wetter diols).

The dressings of the invention may be made by any convenient process, for example a film of, for example hydrophilic polyurethane may be roller printed or hand printed with a pattern of adhesive. Alternatively any other convenient method of providing a non-continuous adhesive may be employed. The coated films may then be cut, packaged and sterilised in conventional manner, for example by irradiation, heat or ethylene oxide.

In a favoured aspect this invention provides a dressing as hereinbefore described in sterile form. Most aptly the sterile dressing is packaged in a bacteria-proof package such as a paper or aluminium foil pouch.

Suitable polyurethane may be produced by the methods of British Patent Specification No. 2093190A and incorporated herein by cross reference are page 6 line 35 to page 8 line 41 thereof.

Normally the dressings are provided for use with a silicone release paper to protect the adhesive which protector is removed prior to use of the dressing.

The following Examples illustrate the invention:

DESCRIPTION

"Dry" MVP Determination

Discs of the material under test are clamped over Payne Permeability Cups (flanged metal cups) using sealing rings and screw clamps. The exposed surface area of the test sample is 10 cm$^2$. Each cup contains approximately 10 ml. of distilled water.

After weighing the cups are placed in a fan assisted electric oven which is maintained at 37±1° C. The relative humidity within the oven is maintained at approximately 10% by placing 1 Kg. of anhydrous 3–8 mesh calcium chloride on the floor of the oven.

The cups are removed after 24 hours, allowed to cool for 20 minutes and re-weighed. The MVP of the test material is calculated from the weight loss and expressed in units of grams of weight per square meter per 24 hours.

"Wet" MVP determination

The method described above is employed except that the Payne Cups are inverted in the oven so that the water within the cups is in contact with the test material.

EXAMPLE 1

Preparation of Film

A solution of a hydrophilic polyurethane (of Example 2 of UK No. 2093190A) in industrial methylated spirits (18% solids) was cast using a doctor blade onto a silicone treated release paper to produce a coating weight after drying of 30±3 g/m$^2$. The cast film was dried at 80° C. to remove solvent.

Pattern Spreading of Film with Adhesive

A solution of acrylic adhesive in acetone (solids content 35%) was coated directly onto the film of hydrophilic polyurethane using an engraved roller so as to produce a reticulated (cross hatched) coating of adhesive. After coating the adhesive was allowed to dy in air before a silicone treated paper protector was applied. The average weight of the adhesive coating was 30±3 g/m$^2$. The area of film covered by the adhesive was approximately 50% of the total available area. (The adhesive was that of Example 1 of European Patent Application No. 81300847.1).

The dry-MVP of the product of this Example was 1250 g/m$^2$ and the wet-MVP was 3600 g/m$^2$ (compare corresponding values of about 1100 g/m$^2$ and about 1250 g/m$^2$ for an analogous material which employed Estate 5714—a non-hydrophilic polyurethane in place of the hydrophilic polyurethane).

EXAMPLE 2

The product of Example 1 was cut into 10×10 cm squares and sealed into pouches. The product was sterilised using ethylene oxide. The resulting sterile dressing may be employed to cover wounds.

EXAMPLE 3

The procedures of Examples 1 and 2 may be carried out replacing the hydrophilic polyurethane by those of British Patent Specification No. 2093190A at page 6 line 35 to page 7 line 25. The resulting dressings are suitable for covering wounds.

EXAMPLE 4

The procedures of Examples 1 and 2 may be repeated using a vinyl ethyl ether adhesive in place of the acrylic adhesive. The resulting dressings may be employed to cover wounds.

EXAMPLE 5

A 25 micron film of polyether polyamide block copolymer (Pebax 4011 supplied by ATO Chemical Products, Newbury, UK) had applied thereto by roller a cross hatched pattern of polyvinyl ethyl ether adhesive. The adhesive covered about 75% of area of the film surface and the diamond shaped interstices accounted for about 25% of the area of the film. The average weight of the adhesive layer was approximately 60 gsm. The resulting material was cut into 15 cm×15 cm squares, placed on silicone release paper (adhesive side to release layer), placed in pouches and sterilised using ethylene oxide.

The dressing had a dry-MVP of about 1800 g/m$^2$ and a wet-MVP of greater than 5000 g/m$^2$.

What is claimed is:

1. A surgical dressing suitable for use on exuding wounds and on non-exuding wounds which consists essentially of a film which carries an adhesive layer for securing the dressing to the body wherein
    (a) the film is continuous and comprises a polymer which in contact with water has a higher MVP than when in contact with moisture vapour but not water and
    (b) the adhesive layer is adapted to allow access of water to the film when water is in contact with the adhesive layer so that
    (c) said surgical dressing has a MVP of not less than 2500 g/m$^2$ when the adhesive layer is in contact with water and has a MVP of not more than 2000 g/m$^2$ when the adhesive is in contact with moisture vapour but not water.

2. A dressing according to claim 1 wherein the MVP is not more than 1500 g/m$^2$ when the adhesive layer is in contact with moisture vapour but not water.

3. A dressing according to claim 2 wherein the MVP is not less than 3200 g/m$^2$ when the adhesive layer is in contact with water.

4. A dressing according to claim 1 wherein the film comprises a hydrophilic polyurethane which when hydrated contains 5% to 50% of water and is from 15 to 80 microns thick.

5. A dressing according to claim 4 wherein the film comprises a hydrophilic polyurethane which when hydrated contains 10% to 40% of water and is from 20 to 60 microns thick.

6. A dressing according to claim 1 wherein the film is a hydrophilic polyurethane which is a hydrophilic polyether polyurethane.

7. A dressing according to claim 1 wherein the adhesive is an interrupted layer which leaves 30% to 70% of the film free of adhesive.

8. A dressing according to claim 1 wherein the adhesive comprises a polyvinyl ethyl ether or an acrylate surgical adhesive.

9. A dressing according to claim 1 in which the average weight per unit area of adhesive is 20 g/m$^2$ to 45 g/m$^2$.

10. A dressing according to claim 1 in sterile form packaged in a bacteria proof package.

* * * * *